(12) United States Patent
He

(10) Patent No.: US 12,011,311 B2
(45) Date of Patent: Jun. 18, 2024

(54) AUTOMATIC ORGAN PROGRAM SELECTION METHOD, STORAGE MEDIUM, AND X-RAY MEDICAL DEVICE

(71) Applicant: Siemens Healthcare GmbH, Erlangen (DE)

(72) Inventor: Wei He, Shanghai (CN)

(73) Assignee: Siemens Healthineers AG, Erlangen (DE)

( * ) Notice: Subject to any disclaimer, the term of this patent is extended or adjusted under 35 U.S.C. 154(b) by 391 days.

(21) Appl. No.: 17/426,720

(22) PCT Filed: Jan. 23, 2020

(86) PCT No.: PCT/EP2020/051608
§ 371 (c)(1),
(2) Date: Jul. 29, 2021

(87) PCT Pub. No.: WO2020/156918
PCT Pub. Date: Aug. 6, 2020

(65) Prior Publication Data
US 2022/0096040 A1    Mar. 31, 2022

(30) Foreign Application Priority Data
Jan. 30, 2019    (CN) .......................... 201910090934.1

(51) Int. Cl.
*A61B 6/00*    (2006.01)
*A61B 6/08*    (2006.01)
*G16H 30/40*    (2018.01)

(52) U.S. Cl.
CPC ............... *A61B 6/545* (2013.01); *A61B 6/08* (2013.01); *G16H 30/40* (2018.01)

(58) Field of Classification Search
CPC .. A61B 6/00; A61B 6/08; A61B 6/545; A61B 6/465; A61B 6/54; A61B 6/542; G16H 30/40; G16H 40/60
See application file for complete search history.

(56) References Cited

U.S. PATENT DOCUMENTS

2013/0083894 A1    4/2013    Niebler et al.
2015/0104092 A1    4/2015    Flohr et al.
(Continued)

FOREIGN PATENT DOCUMENTS

| CN | 104545969 A | 4/2015 |
| CN | 107392897 A | 11/2017 |
| EP | 3582227 A1 | 12/2019 |

OTHER PUBLICATIONS

Notification of Transmittal of the International Search Report and The Written Opinion of the International Searching Authority, or the Declaration dated Apr. 28, 2020, Application No. PCT/EP2020/051608.

*Primary Examiner* — Jurie Yun
(74) *Attorney, Agent, or Firm* — Banner & Witcoff Ltd.

(57) ABSTRACT

The present disclosure relates to an automatic organ program selection method, a storage medium, and an X-ray medical device. According to an implementation, an automatic organ program selection method for X-ray imaging comprises: acquiring an image of a person to be detected; performing organ detection based on the image of the person to be detected, so as to determine an organ to be detected; providing organ programs to be selected that correspond to the organ to be detected; and determining an organ program for the organ to be detected so as to perform X-ray imaging. The present disclosure can greatly reduce the time for setting a system, and reduce the impact of patient movement on determination of an organ program, thereby improving examination efficiency.

9 Claims, 3 Drawing Sheets

(56) References Cited

U.S. PATENT DOCUMENTS

2016/0374639 A1 12/2016 Becker et al.
2019/0021677 A1 1/2019 Grbic et al.
2019/0380806 A1 12/2019 Spahn et al.

AUTOMATIC ORGAN PROGRAM SELECTION METHOD, STORAGE MEDIUM, AND X-RAY MEDICAL DEVICE

CROSS-REFERENCE TO RELATED APPLICATIONS

The present application is a national stage entry of PCT application no. PCT/EP2020/051608, filed on Jan. 23, 2020, which claims the benefit of the filing date of China patent application no. CN 201910090934.1, filed on Jan. 30, 2019, the contents of each of which are incorporated herein by reference in their entireties.

TECHNICAL FIELD

The present disclosure relates to the technical field of medical appliances, and in particular to an automatic organ program selection method for X-ray imaging, a storage medium, and an X-ray medical device.

BACKGROUND

In the process of performing examination by using an X-ray, it usually takes time to position a patient. In addition, the interaction with an X-ray medical system also takes much time, for example, adjusting the X-ray medical system and setting a parameter therefor, etc.

For different organs to be detected (large organs such as the chest, abdomen, and spine, or small organs such as the hand and foot), different examination modes need to be set for the X-ray medical system. An operator needs to select and configure different examination modes for an organ to be detected and the position of the organ. These steps need to be manually completed by the operator, which takes a relatively long time. In practice, these steps are often performed after the patient is positioned, while the patient often moves, and consequently, the related operations are repeatedly performed.

Therefore, there is a need for an automatic organ program selection method that can help reduce the time and effort required for positioning.

SUMMARY

In view of this, the present disclosure provides an automatic organ program selection method for X-ray imaging, further provides a computer storage medium, and still further provides an X-ray medical device.

According to an implementation, the automatic organ program selection method for X-ray imaging of the present disclosure comprises: acquiring an image of a person to be detected; performing organ detection based on the image of the person to be detected, so as to determine an organ to be detected; providing organ programs to be selected that correspond to the organ to be detected; and determining an organ program for the organ to be detected so as to perform X-ray imaging.

The organ detection is performed in real time; or motion detection is performed on the person to be detected, and the organ detection is performed when the person to be detected is not in motion.

Performing the organ detection based on the image of the person to be detected so as to determine the organ to be detected comprises: by using a trained algorithm model and based on information of organs in the image of the person to be detected, preliminarily determining the organs; and determining the organ to be detected from the preliminarily determined organs based on a predetermined condition.

The predetermined condition is: if there is one preliminarily determined organ, determining the preliminarily determined organ as the organ to be detected; and if there are a plurality of preliminarily determined organs, determining an organ in the preliminarily determined organs that is closer to the center of an X-ray beam to serve as the organ to be detected.

According to an implementation, the computer storage medium of the present disclosure stores a program instruction, and the program instruction can be run (e.g. executed by one or more processors) to implement the method as described above.

According to an implementation, the X-ray medical device of the present disclosure comprises: a photographing unit for acquiring an image of a person to be detected; a control unit configured to: perform organ detection based on the image of the person to be detected, so as to determine an organ to be detected; provide organ programs to be selected that correspond to the organ to be detected; and determine an organ program for the organ to be detected so as to perform X-ray imaging.

The organ detection is performed in real time; or motion detection is performed on the person to be detected, and the organ detection is performed when the person to be detected is not in motion.

The control unit is further configured to: by using a trained algorithm model and based on information of organs in the image of the person to be detected, preliminarily determine the organs; and determine the organ to be detected from the preliminarily determined organs based on a predetermined condition.

The predetermined condition is: if there is one preliminarily determined organ, determining the preliminarily determined organ as the organ to be detected; and if there are a plurality of preliminarily determined organs, determining an organ in the preliminarily determined organs that is closer to the center of an X-ray beam to serve as the organ to be detected.

The present disclosure provides an automatic organ program selection method for X-ray imaging, a storage medium, and an X-ray medical device, which can greatly reduce the time for setting a system, and reduce the impact of patient movement on determination of an organ program, thereby improving examination efficiency.

BRIEF DESCRIPTION OF THE DRAWINGS

The above and other features and advantages of the present disclosure will be more apparent to those of ordinary skill in the art from the detailed description of embodiments of the present disclosure with reference to the accompanying drawings below, in which.

Figure 1:
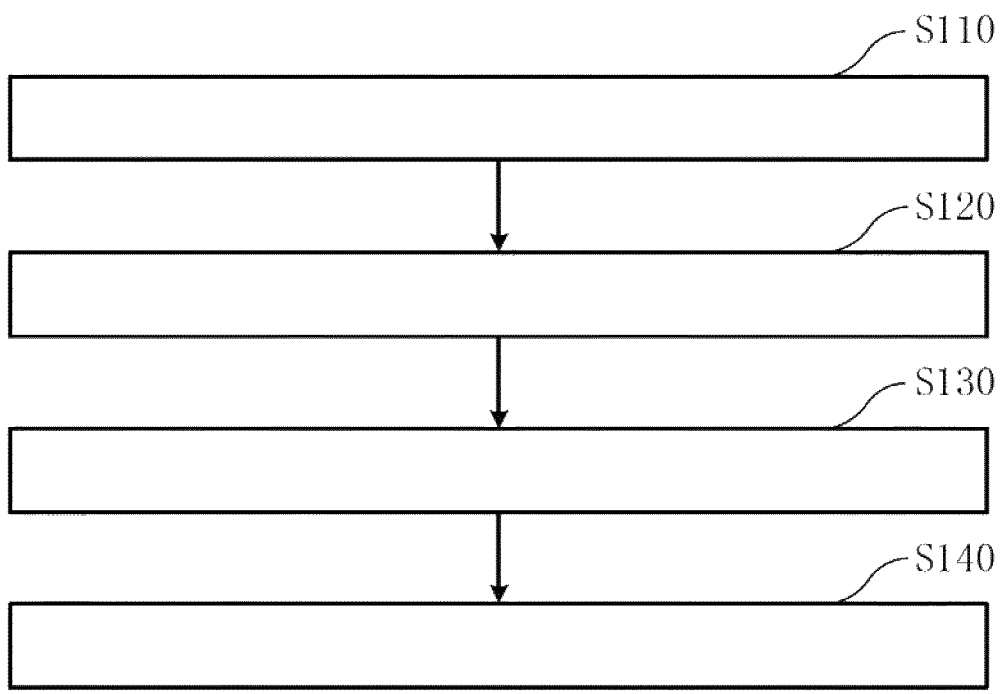
FIG. 1 is a schematic flowchart of an example automatic organ program selection method for X-ray imaging according to an embodiment of the present disclosure.

In the features, reference numerals are as follows:

| | |
|---|---|
| 100 | Method |
| S110-S140 | Steps |
| 300 | X-ray medical device |
| 310 | Photographing unit |
| 320 | Control unit |

DETAILED DESCRIPTION

In order to have a clearer understanding of the technical features, objectives and effects of the present disclosure, specific implementations of the present disclosure are now described with reference to the accompanying drawings, in which like reference numerals refer to like parts.

The word "exemplary" represents "serving as an instance, example or description" herein, and any illustration and implementation described as "exemplary" herein should not be interpreted as a more preferred or more advantageous technical solution.

In order to make the figures concise, the parts relevant to the present disclosure are merely shown illustratively in the figures, and they do not represent the actual structure as a product thereof. In addition, in order to make the drawings concise and easy to understand, in some drawings, only one of the components having the same structure or function is schematically shown or only one of them is marked.

Herein, "a" and "an" not only means "only one", but can also mean "more than one".

First, with reference to FIG. 1, FIG. 1 is a schematic flowchart of an automatic organ program selection method for X-ray imaging according to an implementation of the present disclosure. In the implementation shown in FIG. 1, an automatic organ program selection method 100 for X-ray imaging comprises:

step S110: acquiring an image of a person to be detected;
step S120: performing organ detection based on the image of the person to be detected, so as to determine an organ to be detected;
step S130: providing organ programs to be selected that correspond to the organ to be detected; and
step S140: determining an organ program for the organ to be detected so as to perform X-ray imaging.

Figure 2A:
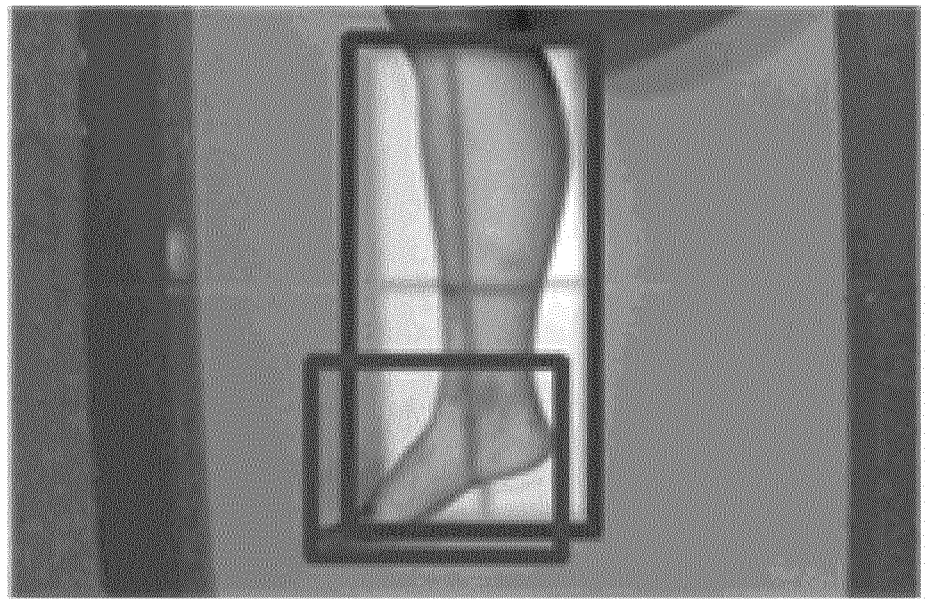
FIG. 2A is a schematic diagram illustrating an example organ contour mask mode according to an embodiment of the present disclosure.
Figure 2B:
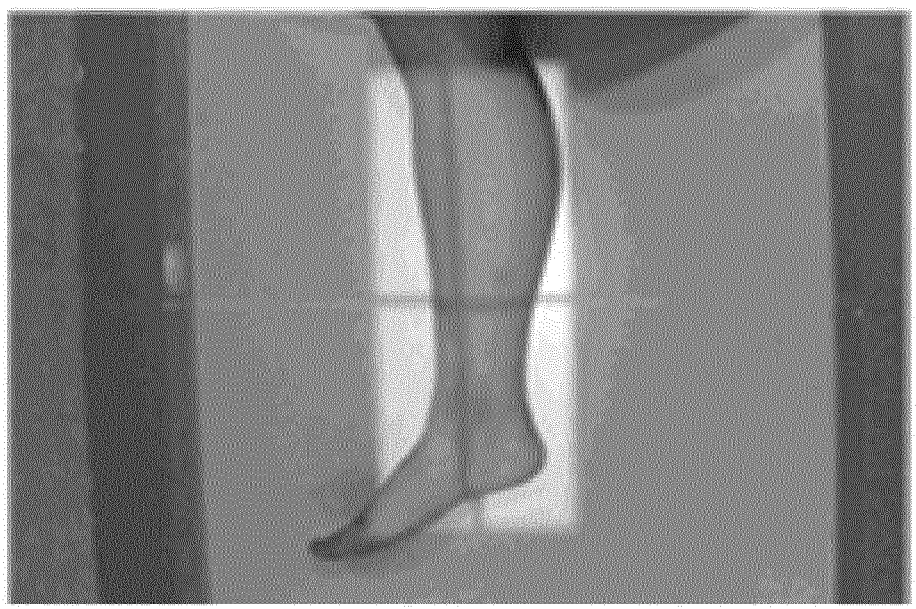
FIG. 2B is an example schematic diagram illustrating a bounding box mode according to an embodiment of the present disclosure.

In step S110, an image of a person to be detected is acquired. The image may be a video, or an image, and the present disclosure is not limited in this respect. In step S120, organ detection is performed based on the image of the person to be detected, so as to determine an organ to be detected. In this implementation, information, such as an organ type and an organ position, of the organ to be detected can be determined by means of organ detection, and optional different organ display modes can be provided, for example, an organ contour mask mode and a bounding box mode, which are respectively seen in FIGS. 2A and 2B. FIG. 2A is a schematic diagram illustrating the organ contour mask mode, and FIG. 2B is a schematic diagram illustrating the bounding box mode.

In step S130, organ programs to be selected that correspond to the organ to be detected are provided. In this implementation, the organ program to be selected can be provided on an operation interface of an X-ray medical device for selection and confirmation by an operator. In step S140, an organ program for the organ to be detected is determined so as to perform X-ray imaging. It can be seen therefrom that, in the automatic organ program selection method for X-ray imaging of the present disclosure, the organ to be detected can be automatically recognized, and the operator only needs to make a final selection and confirmation, thereby greatly simplifying and facilitating operations and saving time.

In an implementation, the organ detection can be performed in real time. Alternatively, motion detection can be performed on the person to be detected, and the organ detection can be performed when the person to be detected is not in motion.

In an implementation, performing the organ detection based on the image of the person to be detected so as to determine the organ to be detected comprises: by using a trained algorithm model and based on information of organs in the image of the person to be detected, preliminarily determining the organs; and determining the organ to be detected from the preliminarily determined organs based on a predetermined condition. It would be readily understood by those skilled in the art that the trained algorithm model refers to an algorithm that has been trained in advance with various related images. In addition, those skilled in the art can extract the contour of the organs in the image of the person to be detected, by using image processing techniques such as contour recognition, to serve as the information of the organs, so as to preliminarily determine the organ therefrom, which will not be described in detail in the present disclosure. In a further implementation, if there is one preliminarily determined organ, determining the preliminarily determined organ as the organ to be detected; and if there are a plurality of preliminarily determined organs (i.e., two or more organs), determining an organ in the preliminarily determined organs that is closer to the center of an X-ray beam to serve as the organ to be detected.

With reference to FIG. 2A, in an implementation shown in FIG. 2A, by using the trained algorithm model and based on the contour of the organs in the image of the person to be detected, the organs are preliminarily determined as the leg and foot. In this case, there are a plurality of preliminarily determined organs (i.e., not a single organ), and therefore, it is required to determine, based on the predetermined condition, which organ in the preliminarily determined organs (the leg and the foot) as the organ to be detected. For example, the predetermined condition may be set as: determining an organ in the preliminarily determined organs that is closer to the center of an X-ray beam to serve as the organ to be detected. "The center of the X-ray beam" may be understood as the center of a plane (i.e., an imaging area) of an imaging apparatus of an X-ray medical device (for example, a detector of the X-ray medical device) that receives the X-ray. In practice, the position of the "center of the X-ray beam" on an imaging side may be determined by means of laser positioning. Specifically, in the implementation shown in FIG. 2A, the position of a cross center formed by two transverse and longitudinal laser lines shown in FIG. 2A is the position corresponding to the center of the X-ray beam, and it can be determined, by determining the distances between the geometric centers of areas in which the two organs of the leg and the foot are located and the center of the X-ray beam, which organ is closer to the center of the X-ray beam. In a particular situation, the distance between a geometric center of an area in which an organ is located and the center of the X-ray beam may be zero, that is, the geometric center coincides with the center of the X-ray beam in this case. It would be readily understood by those skilled in the art that the predetermined condition may be selected and set according to actual needs, and is not limited herein.

Figure 3:
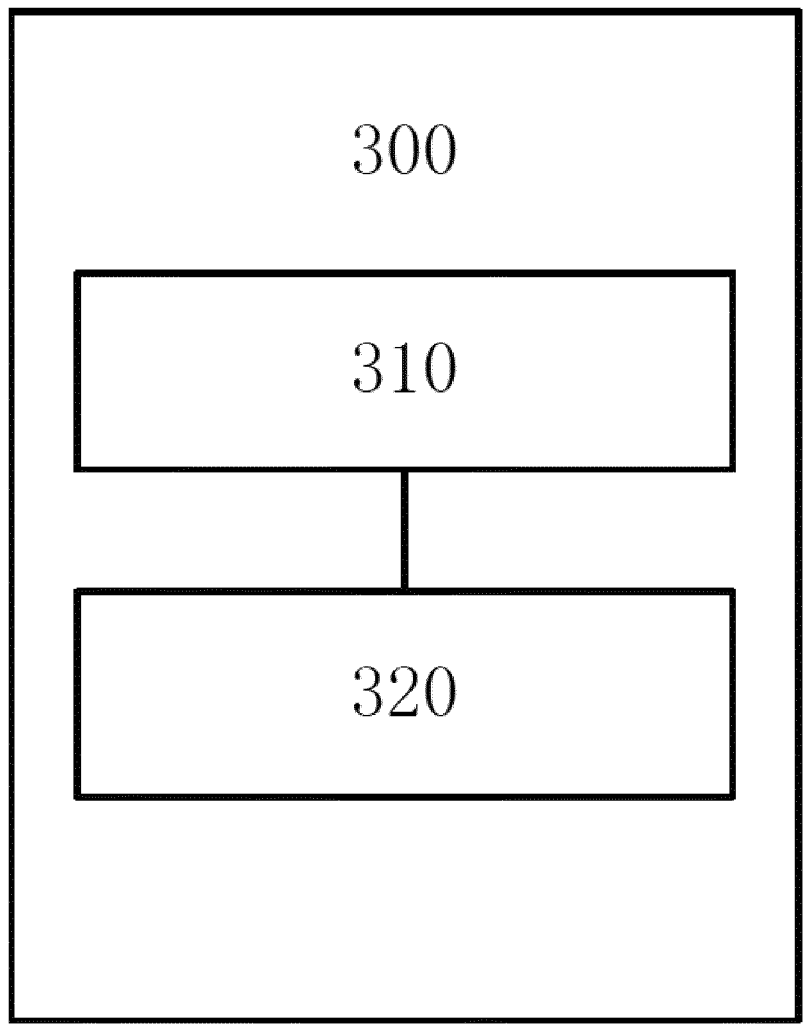
FIG. 3 is an example schematic block diagram of an X-ray medical device according to an embodiment of the present disclosure.

The present disclosure further provides an X-ray medical device. with reference to FIG. 3, FIG. 3 is a schematic block diagram of an X-ray medical device according to an implementation of the present disclosure. An X-ray medical device 300 comprises a photographing unit 310 (e.g. photographing circuitry) and a control unit 320 (e.g. a control computer or processing circuitry). The photographing unit 310 is used for acquiring an image of a person to be detected, and the control unit 320 is configured to: perform organ detection based on the image of the person to be detected, so as to determine an organ to be detected; provide organ programs to be selected that correspond to the organ to be detected; and determine an organ program for the organ to be detected so as to perform X-ray imaging.

In an implementation, the organ detection can be performed in real time. Alternatively, motion detection can be performed on the person to be detected, and the organ detection can be performed when the person to be detected is not in motion.

In an implementation, the control unit 320 is further configured to: by using a trained algorithm model and based on information of organs in the image of the person to be detected, preliminarily determine the organs; and determine the organ to be detected from the preliminarily determined organs based on a predetermined condition. In a further implementation, the predetermined condition may be: if there is one preliminarily determined organ, determining the preliminarily determined organ as the organ to be detected; and if there are a plurality of preliminarily determined organs, determining an organ in the preliminarily determined organs that is closer to the center of an X-ray beam to serve as the organ to be detected.

Furthermore, the present disclosure further provides a computer storage medium, wherein the computer storage medium stores a program instruction, the program instruction can be run to implement any of the above-mentioned methods, and the method previously described can be applied to any of the medical devices disclosed in the present disclosure. Specifically, a system or apparatus with a storage medium may be provided, and software program codes for implementing the functions of any of the above-mentioned implementations are stored on the storage medium, and a computer (or CPU or MPU) of the system or apparatus is caused to read out and execute the program codes stored in the storage medium.

In this case, the program codes per se read from the storage medium may implement the functions of any of the above-mentioned implementations, and therefore the program codes and the storage medium storing the program codes constitute a part of the present disclosure.

The embodiments of the storage medium for providing the program codes comprise a floppy disk, a hard disk, a magnetic optical disc, an optical disc (such as CD-ROM, CD-R, CD-RW, DVD-ROM, DVD-RAM, DVD-RW and DVD+RW), a magnetic tape, a non-volatile memory card and ROM. Optionally, the program codes may be downloaded from a server computer via a communication network.

In addition, it should be clear that the operating system operating on a computer may be caused to accomplish some or all of the actual operations not only by executing the program codes read out by the computer, but also based on an instruction of the program codes, thereby implementing the functions of any of the above-mentioned implementations.

In addition, it can be understood that the program codes read out from the storage medium are written into a memory provided in an expansion board inserted into the computer or written into a memory provided in an expansion unit connected to the computer, then a computing unit such as a CPU installed on the expansion board or the expansion unit is caused to execute some or all of the actual operations based on an instruction of the program codes, thereby implementing the functions of any of the above-mentioned implementations.

The present disclosure relates to an automatic organ program selection method for X-ray imaging, a storage medium, and an X-ray medical device. According to an implementation, an automatic organ program selection method for X-ray imaging comprises: acquiring an image of a person to be detected; performing organ detection based on the image of the person to be detected, so as to determine an organ to be detected; providing organ programs to be selected that correspond to the organ to be detected; and determining an organ program for the organ to be detected so as to perform X-ray imaging. The present disclosure can greatly reduce the time for setting a system, and reduce the impact of patient movement on determination of an organ program, thereby improving examination efficiency.

The above description is only embodiments of the present disclosure and is not intended to limit the present disclosure, and any modifications, equivalent replacements, improvements, etc. made within the spirit and principles of the present disclosure should be included within the scope of protection of the present disclosure.

The invention claimed is:

1. An automatic organ program selection method for X-ray imaging, comprising:
   acquiring, via one or more processors, an image of a person to be detected;
   performing, via the one or more processors, organ detection based on the image of the person to be detected to determine an organ to be detected by (i) performing a preliminary determination of organs to be detected using a trained algorithm model and based on information of organs in the image of the person to be detected, and (ii) determining the organ to be detected from the preliminarily determined organs based on a predetermined condition;
   providing, via the one or more processors, organ programs to be selected that correspond to the organ to be detected; and
   determining, via the one or more processors, an organ program for the organ to be detected to perform X-ray imaging,
   wherein the predetermined condition comprises:
      if there is one preliminarily determined organ, determining the preliminarily determined organ as the organ to be detected; and
      if there are a plurality of preliminarily determined organs, determining an organ from among the preliminarily determined organs that is closer to a center of an X-ray beam as the organ to be detected.

2. The automatic organ program selection method for X-ray imaging of claim 1, wherein the organ detection is performed in real time.

3. The automatic organ program selection method for X-ray imaging of claim 1, further comprising:
   performing motion detection on the person to be detected, and
   wherein the performing the organ detection comprises performing the organ detection when the person to be detected is not in motion based upon the motion detection.

4. A non-transitory computer-readable storage medium storing program instructions thereon that, when executed by one or more processors, cause the one or more processors to perform an automatic organ program selection for X-ray imaging by:
  acquiring an image of a person to be detected;
  performing organ detection based on the image of the person to be detected to determine an organ to be detected by (i) performing a preliminary determination of organs to be detected using a trained algorithm model and based on information of organs in the image of the person to be detected, and (ii) determining the organ to be detected from the preliminarily determined organs based on a predetermined condition;
  providing organ programs to be selected that correspond to the organ to be detected; and
  determining an organ program for the organ to be detected to perform X-ray imaging,
  wherein the predetermined condition comprises:
    if there is one preliminarily determined organ, determining the preliminarily determined organ as the organ to be detected; and
    if there are a plurality of preliminarily determined organs, determining an organ from among the preliminarily determined organs that is closer to a center of an X-ray beam as the organ to be detected.

5. The non-transitory computer-readable storage medium of claim 4, wherein the instructions, when executed by the one or more processors, cause the one or more processors to perform the organ detection in real time.

6. The non-transitory computer-readable storage medium of claim 5, wherein the instructions, when executed by the one or more processors, cause the one or more processors to perform motion detection on the person to be detected, and to perform the organ detection when the person to be detected is not in motion based upon the motion detection.

7. An X-ray medical device, comprising:
  photographing circuitry configured to acquire an image of a person to be detected; and
  control circuitry configured to:
    perform organ detection based on the image of the person to be detected to determine an organ to be detected by (i) performing a preliminary determination of organs to be detected by using a trained algorithm model and based on information of organs in the image of the person to be detected, and (ii) determining the organ to be detected from the preliminarily determined organs based on a predetermined condition;
    provide organ programs to be selected that correspond to the organ to be detected; and
    determine an organ program for the organ to be detected to perform X-ray imaging,
  wherein the predetermined condition comprises:
    if there is one preliminarily determined organ, determining the preliminarily determined organ as the organ to be detected; and
    if there are a plurality preliminarily determined organs, determining an organ from among the preliminarily determined organs that is closer to a center of an X-ray beam as the organ to be detected.

8. The X-ray medical device of claim 7, wherein the control circuitry is configured to perform the organ detection in real time.

9. The X-ray medical device of claim 7, wherein the control circuitry is configured to perform motion detection on the person to be detected, and to perform the organ detection when the person to be detected is not in motion based upon the motion detection.

* * * * *